(12) United States Patent
Davis et al.

(10) Patent No.: US 6,743,583 B2
(45) Date of Patent: Jun. 1, 2004

(54) IDENTIFICATION OF DRUGS AND DRUG TARGETS BY DETECTION OF THE STRESS RESPONSE

(75) Inventors: Ronald W. Davis, Palo Alto, CA (US); Guri N. Giaever, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/898,745

(22) Filed: Jul. 3, 2001

(65) Prior Publication Data

US 2002/0090620 A1 Jul. 11, 2002

Related U.S. Application Data

(60) Provisional application No. 60/218,288, filed on Jul. 14, 2000.

(51) Int. Cl.[7] .............. C12Q 1/68; C12Q 1/02; G01N 33/53; G01N 33/567; C12N 1/20; C12N 1/14; C12N 1/16; C12N 1/18
(52) U.S. Cl. .............. 435/6; 435/7.1; 435/7.2; 435/29; 435/252.3; 435/254.2; 435/455
(58) Field of Search .............. 435/6, 7.1, 7.2, 435/29, 252.3, 254.2, 455

(56) References Cited

U.S. PATENT DOCUMENTS 6,333,155 B1 * 12/2001 Lockhart et al. .............. 435/6

OTHER PUBLICATIONS

Gotthardt, R. et al., "The anti–cancer drug cisplatin induces H25 in Ehrlich ascites tumor cells by a mechanism different from transcriptional stimulation influencing predominantly H25 translation", Int. J. Cancer, vol. 66, pp. 790–795 (1996).*

Bianchi, A.A. et al., "Stress Responses as a Tool to Detect and Characterize the Mode of Action of Antibacterial Agents", Appl. Environ. Microbiol., vol. 65, pp. 5023–5027 (Nov. 1999).*

Adams, C. C. et al., "The Yeast Heat Shock Response is induced by Conversion of Cells to Spheroplasts and by Potent Transcriptional Inhibitors", J. Bacteriol., vol. 173, pp. 7429–7435 (1991).*

Giaever, G. et al. (1999) *Nature Genet.* 21(3):278–283.
Goffeau, A et al. (1996) *Science* 274:563–567.
Marton, M.J. et al. (1998) *Nature Med.* 4:1293–1301.
Rine, J. (1991) *Methods Enzymol.* 194:239–251.
Rine, J. et al. (1983) *Proc. Natl. Acad. Sci. USA* 80:6750–6754.
Shoemaker, D.D. et al. (1996) *Nature Genet.* 14:450–456.
Winzeler, E. et al. (1999) *Science* 285:901–906.

* cited by examiner

*Primary Examiner*—Jeffrey Fredman
*Assistant Examiner*—Teresa Strzelecka
(74) *Attorney, Agent, or Firm*—Carol L. Francis; Bozicevic, Field & Francis LLP

(57) ABSTRACT

The invention features methods of high throughput screening of candidate drug agents and rapid identification of drug targets by examining induction of the stress response in a host cell, e.g., the stress response in wildtype host cells and/or in host cells that differ in target gene product dosage (e.g., host cells that have two copies of a drug target gene product-encoding sequence relative to one copy). In general, induction of the stress response in wildtype host cells indicates that a candidate agent has activity of the drug. Induction of a relatively lower or undetectable stress response in a host cell comprising an alteration in gene product dosage indicates that the host cell is drug-sensitive and is altered in a gene product that plays a role in resistance to the drug.

8 Claims, 1 Drawing Sheet

IDENTIFICATION OF DRUGS AND DRUG TARGETS BY DETECTION OF THE STRESS RESPONSE

CROSS-REFERENCE TO RELATED APPLICATION

This application claims the benefit of prior U.S. Provisional Application Ser. No. 60/218,288, filed Jul. 14, 2000, which application is hereby incorporated by reference.

STATEMENT REGARDING GOVERNMENT SUPPORT

This invention was made with Government support under Grant No. HG00198 awarded by the National Institutes of Health. The Government may have certain rights in this invention.

FIELD OF THE INVENTION

This invention relates to methods for high throughput screening of candidate drug compounds, which finds particular use in the rapid and highly sensitive determination of drug bioactivity and drug target identification.

INTRODUCTION

Traditionally the pharmaceutical industry has relied on two principal methods for drug discovery: 1) in vitro, cell-free biochemical assays; and 2) cell-based assays. In in vitro, cell-free biochemical assays, a massive library of compounds is screened against a given target. Biochemical assays identify compounds of interest by detecting the ability of the compound to alter activity of the target (e.g., by decreasing or increasing an enzymatic activity). The rapidity and efficiency of such screening methods have improved with the advent of automated techniques and advances in computer technology, thus facilitating discovery of important drugs (Palmer, 1996 *Nature Biotech.* 14:513–515).

However, the effectiveness of this high throughput approach to drug screening depends on the ability to design bioassays to test the activity of the target in the screen. The choice of target is then limited, in part, by the efficacy of designing a suitable bioassay amenable to automation. This also requires significant a priori knowledge of the target. In addition, initial target selection is biased since investigators are often forced to select possible targets based only upon a combination of hearsay and empirical experience. Once a compound having a desired activity has been discovered using a biochemical in vitro cell-free assay, several caveats remain including whether the compound will interact with the target in vivo as it did in the cell-free in vitro assay, whether the compound will enter the cell to reach the target, whether it will be stable in vivo, and whether the compound will specifically affect the desired target without affecting non-target gene products, either specifically or nonspecifically. In addition, this screening method makes it difficult to study natural broths or drug mixtures where drug concentrations may be too low to detect any alteration in target activity.

In a second drug discovery method, the compounds are screened for a desired effect in a cell-based assay. Unlike in vitro biochemical assays, cell-based assays are based upon the ability of a compound(s) to affect some function or aspect of an entire organism and will identify compounds that have biologically significant effects. Conventional cell-based assays, however, also have limitations. For example, suitable in vivo assays must be designed, limiting the choice of targets. Cell-based assays can result in identification of compounds that non-specifically affect the cells. For example, investigators can use cell-based assays to identify compounds that generally affect cell growth, but since growth inhibitors may affect any of a variety of cell structures or enzymes, the investigators cannot immediately and directly identify the specific target of the inhibitory compound. In these cases, the drug is either used without knowledge of the target, or more likely, is found to be of limited use due to nonspecific cytotoxic effects.

A direct approach for identification of drug targets is based on the notion that dramatically increasing dosage of the target gene (e.g., through the use of multicopy plasmids), and thus overexpressing the target gene product, will confer resistance to certain drugs. Thus, target gene products can be identified by constructing a library of cells, each cell carrying a multiple copy plasmid expressing a different candidate target gene, and growing the library of cells in the presence of drug to select for those recombinant cells that, by virtue of increased dosage of the target gene, exhibit increased resistance to the drug. Evidence that overexpression of a gene can alter its sensitivity to a drug has been demonstrated (see, e.g. Barnes et al. (1984) *Mol Cell. Biol.* 4:2381–88; Rine et al. (1983) *Proc. Natl. Acad. Sci. USA* 80:6750–6754; Rine (1991) *Meth. Enzymol.* 194:239–251).

Although gene overexpression using high copy number plasmids is a powerful technique for identifying gene products of interest, this approach has certain limitations. Gene product overexpression can itself be lethal to a host cell or can significantly alter the cell's usual biological pathways and processes (Liu, H. et al. (1992) *Genetics* 132:665–673). Moreover, the copy number of the plasmid containing the gene of interest is not easily controlled or predictable (Rine, J. (1991), supra). Furthermore, growth under selective conditions, especially for long periods of time (e.g., days to weeks), encourages selection of mutant cells that may be altered in expression of gene products other than the gene product carried on the plasmid (e.g. second site suppressors). Thus, the target gene identified using this selection process does not always identify the true target of the drug. Finally, such gene overexpression assays can be time-consuming, as the method requires additional screening of drug-resistant clones to identify targets.

Another approach, described by Giaever, G. et al. (1999) *Nature Genet.* 21(3):278–283, takes advantage of the observation that the copy number of a gene encoding a drug target directly and sensitively determines the host cell's sensitivity to the drug to the degree that altering the target gene copy number by only one copy (e.g., from two copies to one copy) elicited a detectable phenotypic change (e.g., a change in growth rate or fitness of the strain) in the presence of the drug. Thus, drugs and their target gene products can be identified by, for example, identification of heterozygous deletion strains that exhibit a slower growth rate in the presence of drug relative to wildtype. Furthermore, this genomic approach is parallel and quantitative: all strains, and therefore all targets, are simultaneously measured for drug sensitivities. While this approach is powerful, it requires use of currently costly DNA microarrays as well as upfront determination of drug activities, which, though straightforward, can be time consuming.

Ideally, one would like a highly sensitive method for high-throughput screening of thousands of candidate agents simultaneously, either separately, or in cocktails, which would allow both the determination of whether a candidate agent is active as a drug, and what the target of the drug might be. In short, there is a need in the field for a simple assay that provides information about the drug activity of candidate compounds using a rapid, sensitive and inexpensive global indicator of such activity that can be easily detected. In addition, once this drug activity is determined, it can be used to determination the drug target of the compound. The present invention addresses this problem.

LITERATURE

Targeted selection of recombinant yeast clones encoding drug resistance by dramatically increasing gene dosage is described in Rine, J. et al. (1983) *Proc. Natl. Acad. Sci. USA* 80:6750–6754.; Rine, J. (1991) *Methods Enzymol.* 194:239–251.

Genomic profiling of drug sensitivities via induced haploinsufficiency is described by Giaever, G. et al. (1999) *Nature Genet.* 21(3):278–283.

Analysis of yeast deletion mutants using a molecular bar-coding strategy is described in Shoemaker, D. D. et al. (1996) *Nature Genet.* 14:450–456.

Drug target validation and identification of "off-target" secondary drug effects using DNA microarrays is described by Marton, M. J. et al. (1998) *Nature Med.* 4:1293–1301.

Functional Classification of the *S. cerevisiae* Genome by Gene Deletion and Parallel Analysis in Winzeler, E. et al. (1999) *Science* 285:901–906, see also the Stanford University yeast deletion project worldwide website at stanford.edu/group/yeast_deletion_3.html.

The complete sequence of the genome of *S. cerevisiae* is available from the Stanford University Saccharomyces genome worldwide website at stanford.edu/Saccharomyces, and is discussed in Goffeau, A et al. (1996) *Science* 274:563–567.

SUMMARY OF THE INVENTION

The invention features methods of high throughput screening of candidate drug agents and rapid identification of drug targets by examining induction of the stress response in a host cell. In general, induction of the stress response in wildtype host cells indicates that a candidate agent has activity on the cell. Induction of a relatively lower or undetectable stress response in a host cell comprising an decrease in gene product dosage of a drug target relative to the wildtype state) indicates that the host cell is drug-sensitive and is altered in a gene product that may encode the target because in this case the cell may be too sick to illicit a "healthy" stress response due to the further inhibition of the gene product in the presence of drug. Similarly, induction of a relatively lower or undetectable stress response in a host cell either resistant to drug or carrying an increase in drug copy number (with respect to wildtype) indicates that the host cell is drug resistant relative to wildtype. The induction of the stress response can be assessed using reporter constructs for selected stress response genes, thus facilitating high throughput screening.

One advantage of the invention is that candidate agents having activity as drugs can be rapidly identified by quantitative or qualitative detection of expression of a single gene (e.g., rather than examining the relative expression levels of multiple genes) in an inexpensive and highly sensitive assay.

Another advantage of the invention is that the methods of the invention exploit the stress response, which is normally regarded as unavoidable "background noise," to rapidly identify candidate agents having drug activity and, where desired, identify the target gene products of the drug activity. Importantly, this stress response often clouds interpretation of microarray expression experiments, forcing the sensitivity to be lowered. The present invention exploits the robust stress response of cells to provide a sensitive metric of drug effectiveness.

Another advantage of the invention is that the host cells having varying copy numbers of the target sequences (or which express the target gene product-encoding sequence at varying levels) are easy to construct and collections can be custom designed to screen for drugs that inhibit specific cellular processes and targets. To date over 80% of the complete heterozygous deletion collection have been constructed. Yeast will not only be useful for the identification of antifungals but will also provide a good model system for identification of cellular processes and pathways that yeast share with humans.

Yet another advantage of the invention is that it does not require overexpression of the candidate target gene product sequence, which can be lethal. Moreover, the effect of the drug and identification of deletion strains that carry a deletion for a target gene product can be identified without the need to assess growth rate, i.e., only a snapshot of stress response gene activity is necessary. Thus the test can be conducted very quickly using induced RNA in the presence of stress. For example, Taqman™ assays can be used to detect the response in only a few minutes.

Still another advantage is that the invention can identify multiple targets of a drug. For example, the method of the invention can lead to identification of several different drug-sensitive host cells, each of which contains deletions of a gene that may encode a drug target, thus identifying any multiple targets if they exist.

Still another advantage is that the invention takes advantage of available genomic information. For example, if the complete or partial sequence of a potential target gene(s) is known, then one can readily construct host cells for use in the invention, even if the function of the gene is unknown. In addition, the host cells need not be heterozygotes for a possible target gene. Instead the host cells could carry an increase in gene dosage. In this embodiment, the expectation is that the stress response would be reduced when compared to that of an unaltered host cell.

Another advantage of the invention is that information about the function of unknown genes can be readily attained in an in vivo system. For example, identifying strains that are sensitive or resistant to a known drug may reveal genes not otherwise known to be involved in the same pathway or parallel pathways. Furthermore, large-scale analysis of drug experiments will undoubtedly reveal clustering of experiments with respect to drug classes and, in addition, with respect to groups of genes that may define functional categories, thus aiding in elucidation of pathways. Indeed, each experiment performed in this manner reiterates the previous experiments, and, in this way, will allow the development of a database of stress response profiles. This database in turn will allow the identification of the "best" reporter genes.

The method of the invention is also advantageous in that it allows screening of many potential drug targets simultaneously (e.g. gene products involved in any cellular process such as DNA synthesis, assembly and function of the mitotic apparatus, sterol biosynthesis, cell wall biosynthesis, etc.), rather than testing such targets individually using conventional methods. For example, all possible targets can be tested using a collection of strains having deletions representative of the entire host cell's genome (e.g., using yeast as a host cell). Such a collection of yeast strains is presently under construction, and is over 80% complete. Moreover, the invention allows for the identification of drug targets for known and new compounds alike, as well as the identification of new drugs that inhibit the same target as a known drug. Furthermore, the rapid nature of the method allows for rapid analysis of several different concentrations of the drug or drug candidates.

Another advantage of the invention is that once a target gene product(s) of a known drug is identified, or a target of interest is chosen, the method can be used to identify other drugs that bind that same target gene product(s) and/or affect the same pathway, thereby facilitating development of drugs that have greater specificity for a target gene product and/or target pathway, elicit fewer side effects, and are safe and effective, thus speeding the drug development process.

The method of the invention is also advantageous in that it is extremely sensitive, thus allowing detection of bioactive compounds at very low concentrations of the candidate compound. The invention thus allows discovery of drugs that would previously go undetected, and requires only a very small amount of candidate compound for screening. For example, assays for detection of drugs can be carried out with 100 host cells and possibly with as few as 10 host cells.

Yet another advantage of the invention is that detection of expression levels of a stress response gene (e.g., through use of a reporter gene construct or through direct measurement of induced RNA) is at least an order of magnitude more sensitive relative to conventional drug inhibition assays, e.g., the method of the invention can be used in place of a halo assay for drugs that do not normally result in a detectable zone of inhibition. For example, host cells could be provided in microtiter plates, drug or candidate drug added to a well(s) of the microtiter plate, and a detectable marker associated with expression of a stress response gene(s) detected. The invention thus provides for a quick, inexpensive, simple assay. These assays require only small volumes of compounds and low numbers of host cells (e.g., as few as 100 cells/well or less), and are 1,000 to 10,000 times more sensitive than, for example, halo assays on plates or conventional liquid culture assays.

The invention is also advantageous in that it can facilitate identification of multiple drugs in a mixture or complex mixture of natural origin, even if the drugs within the mixture have different targets or are present in very low concentrations. Furthermore, the method allows identification of the targets of the drugs within these mixtures.

In addition, it should be noted that the invention also provides valuable information in eliminating those compounds that do not exhibit drug activity in a quick, inexpensive assay. In this aspect, the assay avoids investment of time and money into characterization of compounds that will not be good candidates for further drug development.

The method of the invention is also advantageous in that it is readily adapted to high-throughput automation, is highly parallel and quantitative, and is rapid (i.e., assays can be carried out in a few hours or in some cases in a manner of minutes). Moreover, because the assays do not require long term growth (i.e., not more than a few hours) the probability of selection for secondary mutations that might mask the effect of the true target gene is minimized.

Still another advantage of the invention is that it is relatively inexpensive to screen multiple drugs since, for example, collections of strains representing a large number of targets can be screened simultaneously in small culture volumes (100 μl or less), thus requiring only small amounts of drug. In addition, the equipment and supplies needed for this type of assay is minimal; i.e., requiring only off the shelf robotics, microtiter plates, media, and a fluorescent plate reader.

Another advantage of the invention is that it can be readily adapted for use with a wide variety of host cells (e.g., haploid or diploid organisms; bacterial, yeast, or mammalian cells) and with a wide variety of candidate target gene product sequences.

DETAILED DESCRIPTION OF THE INVENTION

Overview

Figure 1:
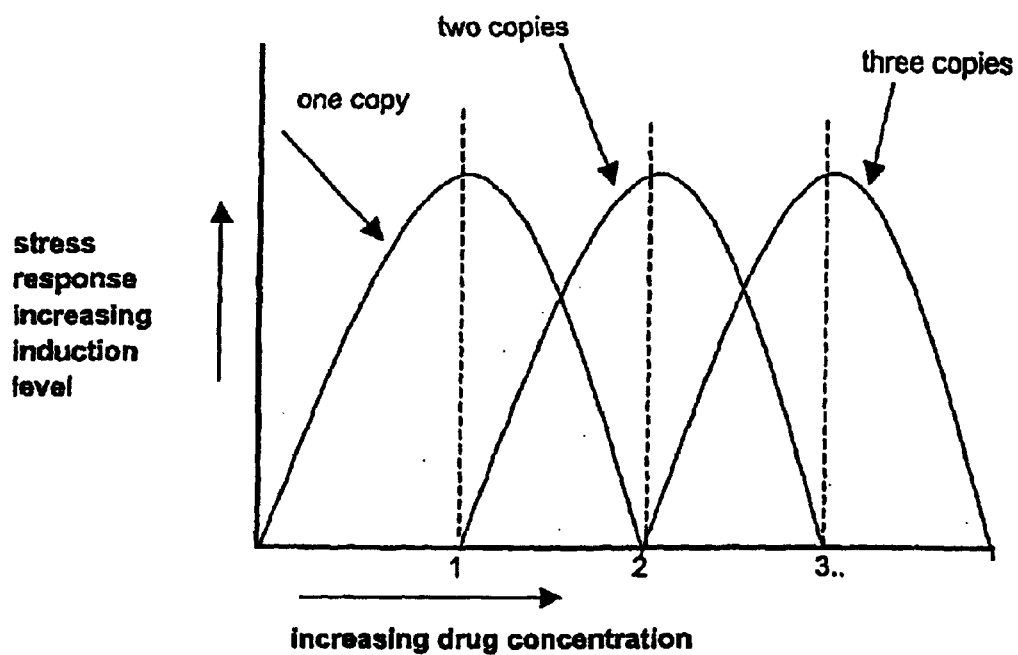
FIG. 1 is a graph illustrating a proposed relationship between the stress response induction level, the copy number of a target gene, and drug concentration.

The invention provides both 1) a method for rapidly identifying compounds that have activity as a drug (i.e., bioactive compound), and 2) a method for identifying the target gene products with which a drug interacts. The invention takes advantage of the inventors' discovery that candidate agents that have drug activity 1) induce a stress response in wildtype host cells, and 2) induce a less robust to undetectable stress response in drug-sensitive host cells relative to wildtype host cells. Without being held to theory, based on this discovery the inventors would expect that candidate agents that have drug activity would not induce a stress response in drug-resistant host cells relative to unaltered host cells, and thus agents with drug activity would induce a greater stress response in host cells relative to, for example, drug-sensitive host cells as well as resistant host cells. Without being held to theory, a relationship between the stress response induction level, the copy number of a target gene, and drug concentration is illustrated in FIG. 1 This phenomenon can be summarized as follows:

TABLE 1

| | heterozygous sensitive strain | wildtype strain | 1 extra copy or resistant strain |
|---|---|---|---|
| drug concentration low | induction high | induction low | induction low |
| drug concentration medium | induction low | induction high | induction low |
| drug concentration high | induction low | induction low | induction high |

The invention takes advantage of this phenomenon to provide for the rapid identification of candidate agents that have activity as drugs (e.g., through examination of the stress response in a wildtype host cell), as well as for the rapid identification of candidate target gene products of drugs (e.g., by identifying a drug-sensitive host cell that exhibits a reduced stress response relative to a wildtype host cell).

Specifically, the invention is based on two discoveries. The first is that stress response genes are induced in a wildtype host cell when exposed to drug. For example, one of the genes exhibiting the greatest induction is the HSP26 gene. The ability of a candidate agent to induce increased expression of HSP26 in a wildtype host cell indicates that the candidate agent has activity as a drug. Screening for induction of HSP26 or other stress response gene can be accomplished by, for example, constructing a green fluorescent protein (GFP) reporter gene using the HSP26 promoter, and transforming this construct into wildtype cells. Induction of HSP26 can then be rapidly assayed by detection of fluorescent signals in wildtype cells.

The second discovery upon which the invention is based is that host cells that are drug sensitive do not elicit a "healthy" stress response compared to wildtype. Instead, stress response genes (e.g., HSP26) are induced at relatively low to undetectable levels in such drug-sensitive host cells. This observation can be exploited to identify the target(s) of drugs or candidate drug agents. For example, a series of heterozygous deletion strains containing a stress response gene reporter construct (e.g., GFP-HSP26 construct) can be prepared, where each heterozygous deletion strain contains a deletion in a different target gene product. Detection of a lower stress response as measured by the stress response reporter gene indicates either that the heterozygous deletion strain contains a deletion in target gene product of the drug or that the target gene product is functionally related to the same pathway as the actual drug target (e.g., a gene acting downstream in the pathway of the drug target, a gene involved in drug availability, etc.).

The method of the invention can be readily adapted to simultaneously identify candidate drugs as inhibitory compounds and identify the target of the candidate drug's inhibitory action. For example, if a candidate drug elicits a lower stress response in a heterozygous deletion strain relative to the stress response of a diploid host cell (e.g., wildtype) or to other heterozygous deletion strains, then the candidate drug has activity toward the target gene product that is altered in the heterozygous deletion strain, e.g., a heterozygous deletion strain exhibiting a decreased stress response relative to wildtype contains a deletion in a target gene product that confers sensitivity to the drug.

The present invention thus provides an elegant, genome-based, specific, parallel and sensitive method for drug discovery and drug target identification. The invention provides an efficient means for identifying candidate agents that are bioactive, and further facilitates the rapid identification of the gene product, system, or pathway affected by the drug activity. The method also provides an efficient method for identifying drugs having activity against a target gene product of interest or against one or more target gene products within a set of target gene products. In addition to drug discovery, the method of the invention has various applications in identification of the target/mechanism of candidate drug action, rational approaches to efficacy improvement, and rapid categorization of compounds as to potential toxicity and possible therapeutic applications. The method of the invention can also provide a means to identify genes that play a role in, or that can influence, a biological process or pathway or interest. Finally, the method of the invention is not limited by the available knowledge of the target genes or of the compounds to be screened. Rather, the claimed invention is useful in identification of targets of known drugs where the target is not known, simultaneous characterization of new drugs and their targets, and screening of a library of drugs (e.g., a mixture of drugs or compounds, natural extracts including those that contain nonspecific toxins, or broths) to identify the affected targets.

In addition, the invention can be used to rapidly determine the optimal drug concentration to facilitate haplo-insufficiency profiling (Giaever G. et al. (1999) Nature Genet. 21:278–283)(e.g., to identify target gene products). Furthermore, by introducing a stress gene reporter construct into an entire collection (e.g., library) of strains having differing expression levels of different possible target genes (e.g., a library of heterozygous deletion strains, each having a deletion in a different gene), the invention can be used to rapidly determine whether a candidate compound has drug activity and, if so, to rapidly identify the target gene products and the gene product(s) involve in the pathway in which the target gene product is involve.

Identification of compounds having drug activity is only one of many possible applications. For example, the invention can be used to monitor other types of stress, such as stress associated with viral infection, changes in environmental conditions (e.g., temperature, osmolarity, etc.), and the presence of toxins (e.g., in biological warfare situations). The invention can also be used to identify compounds that act against microorganisms in biological warfare. Microorganisms used in biological warfare are likely to be resistant to several standard antibiotics. This approach could help to rapidly identify the compounds which could kill the microorganism. The invention can also be used to prescreen compounds for bioactivity prior to their further study to identify their precise target(s) and mode of action. In this way, a rapid prescreen of a 200,000 or greater compound libraries could reduce the volume of compounds that would enter into a screen for further compound characterization.

The invention will now be described in more detail.

Stress Response Genes and Detection Thereof

Numerous stress response genes suitable for use in the invention have been identified; many of these have been cloned, and their promoter and coding sequences determined. Exemplary stress response genes that may be used to detect induction of the stress response in a host cell according to the invention are provided in Table 2 below. The genes listed in the tables below are meant to be exemplary, and are further meant to refer to the genes found in for example, yeast, as well as the homologs found in the selected host cell (e.g., the homolog of the yeast gene found in a mammalian cell, e.g., a human cell; and the like). By "homolog" of a stress response gene is meant a stress response gene or sequence encoding a stress response protein of a different origin (e.g., of mammalian origin) that provides a similar function in the host cell of interest (e.g., a mammalian homolog of a yeast heat shock protein is a mammalian protein that exhibits an expression pattern under the same type of stress (heat) in mammalian cells as in yeast cells).

TABLE 2

Stress Response Gene Families

| Stress Response Gene Family | Exemplary Family Members |
| --- | --- |
| Small Heat Shock Protein (Hsp) Family | AlphaB-Crystallin, AlphaA-Crystallin, GrpE, Hsp25, Hsp27, Hsp30, Hsp26 |
| Other Hsp's and Related Proteins | Cpn10/Hsp10, DnaJ, GroES, Hip, Hsp30, Hsp32 (HO-1), Hsp40, Hsp47, Hsp56, HO-2, Metallothionein, Ubiquitin |

TABLE 2-continued

Stress Response Gene Families

| Stress Response Gene Family | Exemplary Family Members |
|---|---|
| Hsp60/Cpn60 Family | GroEL, Hsp60/Cpn60, Hsp65, TCP-1 (CCT) |
| Chaperone Containing TCP-1 (CCT) | TCP-1 Alpha, TCP-1 Beta, TCP-1 Delta, TCP-1 Epsilon, TCP-1 Eta, TCP-1 Gamma, TCP-1 Theta, TCP-1 Zeta |
| Hsp70 Family | DnaK, ERp72, Grp75 (mtHsp70), Grp78 (BiP), Hsc70 (Hsp73), Hsp70 (Hsp72), Hsp70B', Hsp71, Hsp110 |
| Hsp90 Family | Hsp90 Alpha, Hsp90 Beta, Grp94, Hsp83 |
| Hsp100 | Hsp100, Hsp104 |
| Oxidative Stress | Biliverdin Reductase, Cytochrome P450, Cytochrome P450 Reductase, Glutathione NEM, Heme Oxygenase-1 (Hsp32, HO-1), Heme Oxygenase-2 (HO-2), HSF1, c-Jun, iNOS, eNOS, nNOS, Superoxide Dismutase (Mn) |
| ER Proteins | rbet1, Calnexin, Calreticulin, Erp72, Hsp47 (Colligin), Glucosidase II (alpha), Grp78 (BiP), Grp94, KDEL, Protein Disulfide Isomerase (PDI), UGGT |
| Glucose Regulated Proteins | Grp58, Grp75 (mtHsp70), Grp78 (BiP), Grp94 |
| Stress Activated Kinase Pathway | GCK, HPK-1, JKK1, c-Jun, Mek6, Mekk1, MeKK3, SAPK Alpha, SAPK Beta, SAPK Gamma, Sek1 (MKK4), TAK1, ZPK |

In addition, the following *S. cerevisiae* exemplary specific genes and open reading frames have been identified as being involved in the stress response (Craig, E. A. The Molecular and Cellular Biology of the Yeast Saccharomyces: GENE EXPRESSION 501–538 (Cold Spring Harbor University Press, Cold Spring Harbor, N.Y., 1990).)

TABLE 3

| ORF name | Gene name | GenBank Accession Nos. | Gene description |
|---|---|---|---|
| YBR072W | HSP26 | Z35941 (see also NC_001134) | chaperone |
| YOR020C | HSP10 | Z74928 (see also NC_001147) | chaperone (mitochondrial) |
| YFL014W | HSP12 | D50617 and NC_001138 | chaperone |
| YCR021C | HSP30 | NC_001135 and X59720 | chaperone |
| YDR171w | HSP42 | NC_001136 | chaperone |
| YLR259C | HSP60 | NC_001144 and U17244 | chaperone |
| YDR258C | HSP78 | NC_001136 | chaperone |
| YPL240C | HSP82 | NC_001148 and Z73596 | chaperone |
| YLL026w | HSP104 | NC_001144 and Z73131 | chaperone |
| YAL005C | SSA1 | NC_001133 and L22015 | chaperone |
| YDR059c | UBC5 | CAA89088.1 | protein degradation |
| YMR173w | DDR48 | CAA89906.1 | cell stress; DNA repair |

Table 4 lists those genes that have been identified as being induced in the presence of drugs by the experiments described herein, though not intended to be a complete list. Many of these genes are involved in a stress response as a result of drug treatment. These genes include known stress response genes as well as genes that may not play a direct role in the stress response, i.e., do not facilitate a protective effect for the host cell in the presence of stress, but may instead have their expression "linked" to expression of stress response genes, making them good reporter genes as evidenced by their induction in the presence of drugs or stresses other than tunicamycin (see Table 7). Thus, "stress response gene" as used herein, unless specifically noted otherwise, is intended to encompass genes that are increased in expression when the host cell is subjected to stress, including genes that encode for gene products that protect or defend the host cell from stress as well as genes that do not necessarily encode for stress-protective gene products per se, but that are co-expressed with other stress-protective gene products (e.g., genes that are induced for expression when stress response genes are induced for expression).

TABLE 4

| ORF Name | Gene Name | GenBank Accession Nos. | Gene Description |
|---|---|---|---|
| YBR072W | HSP26 | Z35941 (see also NC_001134) | Chaperone |
| YBL049W | | Z35810 or Y13134 (see also NC_001134) | Unknown |

TABLE 4-continued

| ORF Name | Gene Name | GenBank Accession Nos. | Gene Description |
|---|---|---|---|
| YDR018C | | NC_001136 and Z74314 | lipid, fatty-acid and sterol metabolism |
| YFL030W | | NC_001138 and D50617 | Putative transferase |
| YFL059W | SNZ3 | NC_001138 and D50617 | cell stress |
| YGR043C | | NC_001139 and Z72828 | cell stress, transferase (predicted) |
| YHR096C | HXT5 | NC_001140 and U00060 | Transporter, MFS family, integral membrane |
| YIL042C | | NC_001141 | Transferase (predicted) |
| YIL117C | | NC_001141 | Unknown |
| YJL079C | PRY1 | NC_001142, AW180815 and Z49354 (human homologue at W69382) | cell stress (predicted) |
| YKL107W | | NC_001143 and Z28107 | Unknown |
| YLR053C | | NC_001144 and Z73225 | Unknown |
| YLR121C | YPS3 | NC_001144, U53877, and Z73293 | Protein degradation |
| YLR142W | PUT1 | NC_001144, U53881 and Z73314 | Amino acid metabolism |
| YMR081C | ISF1 | NC_001145 | rna splicing |
| YMR107W | | NC_001145 | Unknown |
| YNL194C | | NC_001146 and Z71470 | cell stress (predicted) |
| YFR026C | | | Unknown |
| YGL156W | AMS1 | | Carbohydrate metabolism |
| YJL144W | | | Unknown |
| YMR040W | | | Unknown |
| YKL104C | GFA1 | | Carbohydrate metabolism, cell wall maintenance |
| YGR032W | GSC2 | | Carbohydrate metabolism, cell membrane maintenance |
| YLR080W | | | Unknown |
| YMR174C | PAI3 | | Protein degradation, cell stress |
| YLR178C | TSI1 | | Protein degradation, cell stress |
| YMR090W | | | Oxidoreductase |
| YLR194C | | | Unknown Localizes to cell wall |

In general, it is preferably to monitor genes that are induced in the presence of stress response (preferably induced under several different stress conditions), but are expressed at significantly lower levels (e.g., are expressed at a low basal level) in the absence of stress, e.g., the fold induction of gene expression in the presence of stress relative to the absence of stress is significant and readily detectable. Of particular interest is detection of expression of Hsp26p, Hsp42p, Yfl030wp, and/or Ynl194 cp proteins for example. See Table 8 for more details.

In one embodiment, the stress response gene is a member of the small heat shock protein family. In a preferred embodiment, expression of the stress response gene HSP26 is detected in the methods of the invention. The promoter and coding sequence of HSP26 of *Saccharomyces cerevisiae* has been isolated and sequenced.

Expression of a selected stress response gene can be detected in a variety of ways well known in the art, e.g., by use of hybridization probes, PCR primers, or antibodies specific for a selected stress response gene product. Kits designed for detection of a variety of different stress response genes are commercially available from companies such as StressGen Biotechnology Corporation (Victoria, Canada). Methods for detecting stress response genes are also described in the art (see, e.g., U.S. Pat. No. 5,807,690), see also Inducing and Assaying Heat-Shock Response in *Saccharomyces cerevisiae*, Nicolet, C. M. and Craig, E. A. *Guide to Yeast Genetics and Molecular Biology* 710–717. Academic Press, Inc., San Diego, Calif., 1991. Editors Guthrie, C. and Fink, G. R.

Reporter Constructs for Detection of Stress Response Induction

In one embodiment, detection of the stress response in the host cell is facilitated by detection of a stress response gene reporter construct. In general, the stress response gene reporter construct (referred to hereafter as "reporter construct" for clarity) minimally comprises a promoter of a stress response gene operably linked to a sequence encoding a reporter polypeptide.

The reporter construct can be introduced into the host cell according to methods well known in the art. The construct can be maintained as an episomal element or integrated into the chromosome of the host cell. Where the reporter construct is present as a chromosomally integrated element, the reporter construct can utilize a native stress response gene promoter, e.g., the reporter construct can be generated by homologous recombination of a sequence encoding a reporter polypeptide into a stress response gene to provide expression of the reporter polypeptide from the endogenous stress response gene promoter. In one embodiment of interest, the construct comprises a native HSP26 promoter operably linked to a sequence encoding a modified GFP protein on a centromere-based plasmid.

Reporter Polypeptide

The reporter polypeptide of the reporter gene construct provides a detectable signal for detection of expression directed by the stress response gene promoter. The reporter polypeptide may directly provide the detectable signal (i.e., the reporter polypeptide may be auto-fluorescent) or may provide the detectable signal after addition of a reagent (e.g., ligand for the reporter polypeptide, detectably labeled anti-reporter polypeptide antibody, etc.). Reporter polypeptides suitable for use with the invention include, but are not necessarily limited to, -galactosidase, luciferase, green fluorescent protein (GFP), and the like. Where the assay is to be conducted with a mixed culture of host cells (e.g., wildtype host cells, various heterozygous deletion strains, and/or host cells having an overexpressed candidate target gene product in a single culture), the reporter polypeptide is preferably retained by the host cells that expresses it (e.g., the reporter polypeptide is not secreted to any significant degree, e.g., the polypeptide is a cytoplasmic protein, a cell surface protein, etc.). In this case, the reporter for, for example, the wildtype host cell would carry a different reporter than that for the heterozygous strain, e.g. GFP and RFP (red fluorescent protein) respectively (both available from Clontech).

In one embodiment, the reporter polypeptide is GFP or a GFP variant. Several GFP variants with distinct fluorescence excitation and emission spectra have been engineered for intended use in multi-labeling experiments (see, e.g., Ellenberg J. (1998) *Biotechniques* 25:838–946; Heim R. et al. (1995) *Nature* 373:663–664; Cormack B. P. et al. (1996) *Gene* 173:33–8; Heim R. et al. (1996) *Curr. Biol.* 6:178–82. Exemplary GFP mutants of interest include, but are not necessarily limited to, GFPuv (Clontech). In another embodiment, the reporter polypeptide is Red Fluorescent Protein (RFP). The invention contemplates the use of a single reporter polypeptide, as well as the use of multiple reporter polypeptides. For example, the use of two reporter polypeptides, e.g., a first reporter polypeptide for a test strain and a second, different reporter polypeptide for a wildtype or other control strain.

Introduction into Host Cells

Methods for introducing a reporter construct into a host cell are well known in the art. This can be accomplished by, for example, introduction of an autonomous plasmid, which can be maintained as an episomal element and/or chromosomally integrated into the genome of the host cell. Suitable constructs, vectors, plasmids, etc. are well known in the art and will vary with the host cell, size and other characteristics of the reporter gene, etc. For example, where the host cell is a yeast cell, suitable autonomous plasmids include, but are not limited to, 2- m circle-based vectors (see, e.g., Rose, A. B. et al., supra; Rose, A. B. et al., supra) centromere-based (Ycp) vectors, and ARS-based vectors (Rose, A. B. et al., supra). For additional yeast vectors useful in the invention, see Yeast Vectors and Assays for Expression of Cloned Genes, Ausubel, F. et al. (1997) in Current Protocols in Molecular Biology Vol.2, John Wiley and Sons, Chapter 13.6.1, Schena, M. et al., supra (describing the pG-1, pG-2, pG-2, and p2UG/pG-N795 expression vector systems). See also Inducing and Assaying Heat-Shock Response in *Saccharomyces cerevisiae*, Nicolet, C. M. and Craig, E. A. (1991) in Guide to Yeast Genetics and Molecular Biology 710–717, Academic Press, Inc., San Diego, Calif., Editors Guthrie, C. and Fink, G. R.

Host Cells

The assay of the invention can be used in connection with any of a variety of host cells, including eukaryotic, prokaryotic, diploid, or haploid organisms. Where the host cell is to be used as the basis for generation of strains having altered levels of expression of a selected gene product (e.g., heterozygous deletion strains or strains having increased levels of a candidate target gene), the host cell is generally one that allows for genetic manipulation to provide for adequately precise regulation of target gene expression (e.g., the copy number of a target gene can be readily manipulated between two copies and one copy and/or the host cell allows for manipulation of transcription levels of a target gene to provided for altered expression levels). Host cells can be single cell organisms (e.g., bacteria, e.g., Mycobacterium spp., e.g., *M. tuberculosis*) or multicellular organisms (transgenic organisms, such as insects (e.g., Drosophila spp), worms (e.g., Caenorhabditis spp, e.g., *C. elegans*) and higher animals (e.g., transgenic mammals such as mice, rats, rabbits, hamsters, humans etc. or cells isolated from such higher animals, including humans). Preferably the host cell is a naturally diploid cell, preferably yeast cells (e.g., Saccharomyces spp. (e.g., *S. cerevisiae*), Candida spp. (e.g., *C. albicans*)) or mammalian cells. The host cell can also be a cell infected with a virus or phage that contains a target sequence in the viral or phage genome.

Yeast is currently a particularly preferred host cell for the method of the invention. Specifically, yeast naturally provides a powerful, easily genetically manipulatable model system that naturally contains target sequences of potential interest. For example, biochemical pathways exclusive to fungi can be enfeebled via gene disruption and potential drugs identified based on increased sensitivity to specific drugs compared with wildtype (Kirsch, D. R. (1993) *Curr. Opin. Biotechnol.* 4(5):543–552). Moreover, because of the extensive homology shared between yeast and human proteins (Foury, F. (1997) *Gene* 195: 1–10), yeast can also be exploited to assay human drug targets by expressing a potential human drug target in the yeast host in lieu of the yeast homolog. Furthermore, identification of a target in yeast that shares homology with a human gene product can also provide information about the interaction the drug with the human homolog. Thus, yeast provide a genetically manipulatable host cell, a genome encoding potentially interesting target sequences, and a system for expression of recombinant sequences, including sequences from other organisms (e.g., human sequences). In addition, yeast can be used to screen compounds against a single desired target gene product of interest.

Strains Having Altered Levels of Expression of a Selected Gene Product

Methods for altering levels of expression of a selected gene product are well known in the art. For example, gene product expression levels can be altered by altering the number of copies of the target gene (e.g., by decreasing target gene copy number (e.g., by deletion or otherwise rendering a target gene copy nonfunctional) or by increasing target gene copy number (e.g., by introducing an additional copy(ies) of the target gene). Alteration of target gene expression can also be accomplished by specifically altering the native promoter of the target gene (e.g., through use of a mutated native promoter or a heterologous promoter, including constitutive and inducible promoters) or by alteration of translation of target gene transcripts. Alteration of target gene expression can also be achieved by construction of strains carrying a conditional mutation in a target gene, where the strain contains, for example, a temperature sensitive mutation in one copy of the target gene, which mutation renders the gene nonfunctional when grown at certain temperature. Alternatively, target gene expression can be altered by expression of antisense RNA to decrease expression of the target sequence. Thus, strains referred to herein as strains having "altered expression levels of a target gene" are thus meant to encompass strains having varying target gene copy number as well as strains containing other genetic alterations that provide for differences in transcription of a specific target sequence, e.g., by introduction of a heterologous promoter that facilitates transcription of the target gene in lieu of the native target gene promoter.

The method of the invention can also be used in conjunction with host cells containing multiple mutations. For example, the strain can contain a "double knock-out," i.e., the strain is deleted for two different genes, and thus is a double heterozygote deletion strain. Since some mutations may only demonstrate an effect in the context of a second mutation, the use of strains containing multiple mutations may reveal additional targets.

Target Genes

The non-wildtype strains used in the method of the invention can be altered in expression (e.g., by altering copy number or otherwise affecting transcription levels) of any gene of interest. As used herein, a "target gene" or "target sequence" is any genomic or episomal sequence encoding any open reading frame, i.e., a sequence encoding a polypeptide (normally of at least about 100 amino acids in length), peptide, oligopeptide, or functional RNA or DNA. As used herein "target sequence copy number" refers to the number of functional target sequences contained and expressed in a host cell. By "functional target sequence" it is normally meant a nucleotide sequence that is expressed in the host cell to provide a functional gene product, i.e., a wildtype gene product that can serve its ordinary structural, enzymatic, or other function in the host cell. Such "functional target sequences" however, could also include non-coding bioactive nucleic acid (DNA or RNA) sequences.

It is not necessary that the function of the product encoded by the target gene be known; rather, the method of the invention can be used to determine whether the encoded unknown gene product plays a role in resistance or sensitivity to drug activity. Thus, the target genes can encode any of a variety of gene products, including, but not limited to, genes encoding a protein having an enzymatic activity, structural genes (i.e., DNA sequences which encode a protein or peptide product), regulatory genes (i.e., DNA sequences which act as regulatory regions, such as promoters, enhancers, terminators, translational regulatory regions, etc., to affect the level or pattern of gene expression), and DNA sequences that encode a bioactive RNA or DNA, such as an antisense RNA (i.e., to provide for inhibition of expression of a host DNA sequence), or structural RNAs (i.e., RNAs with enzymatic activities or binding activities (ribozymes).

The method of the invention is not limited to examination of the role of "essential" genes, i.e., genes that are conventionally thought to be necessary for cell growth under a given condition or set of conditions. Rather, the invention recognizes that the concept of "essential" genes has hindered the discovery of genes with duplicative function or genes in duplicate pathways that can facilitate resistance to drugs that are targeted against "essential" genes. In addition, the invention recognizes that "essential" is a relative term that is dependent on the conditions under which the gene is essential (i.e. some genes nonessential for normal growth in the lab may be essential when grown in a natural habitat). Furthermore, Giaever, G. et al. (1999) Nature Genet. 21:278–283 have shown that nonessential genes can exhibit extreme drug sensitivity. The method of the invention can be used to unmask such "nonessential" genes that encode potential drug targets of interest, thus facilitating the design of drugs that can be used alone or in combination with conventional drugs to minimize selection of resistant strains, reduce the amount of drug or the time of administration necessary to combat disease, and thus provide a means to avoid side effects associated with administration of high dosages or lengthy drug courses (e.g., toxicity to the subject and other side effects).

Construction of Host Cells Containing Different Copy Numbers of Candidate Target Gene Product-Encoding Sequences (e.g., Heterozygous Deletion Strains)

In one embodiment, the method of the invention employs strains having precise, varying copy numbers of the target sequence of interest. In any given strain, the copy number of the target sequence (i.e., the number of functional copies of the target sequence) is preferably either exactly two (i.e., diploid wildtype), exactly one (i.e., heterozygous deletion strain), or exactly three.

Heterozygous deletion strains can be constructed by site-specific deletion of a genomic sequence according to methods well known in the art. The site-specific deletion can be accomplished by using tagged transposons and retrospectively identifying strains containing the tagged transposons inserted into a desired gene. Alternatively, site-specific deletions can be generated using homologous recombination (e.g., Rothstein et al. 1991, supra). Where the host cell is a yeast cell, the heterozygotescan be constructed according to the methods of Rothstein, R. (1991) Meth. Enzymol. 194:281–301, combined with the construction of strains containing molecular tags as per the method of Shoemaker, D. D. et al. (1996) *Nature Genet.* 14:450–456, Winzeler et al. (1999) *Science* 285: 901–906, which involves incorporation of one or two molecular tags during the site-specific deletion process. A wildtype diploid host cell having a tag inserted in a non-functional gene can serve as control or reference strain where desired. For an example of uses of molecular tags in a screening assay, see, e.g., U.S. Pat. No. 6,046,002.

The strains used in the screening method can vary from a single strain altered in expression of a single target gene to a collection of strains representing a selected set of target gene deletions (e.g., a set of genes involved in a selected signaling pathway or members of a selected protein family (e.g., kinases)). In one embodiment, the method of the invention employs a complete genomic set of genetically tailored yeast strains potentially sensitized or resistant to every possible drug target coded by the yeast genome, with each strain carrying a deletion of a single genetic locus. A fifteen-lab international consortium is currently carrying out production of a collection of tagged heterozygous deletion strains. This collection of bar-coded deletions is available at the Stanford University yeast deletion project worldwide website at stanford.edu/group/yeast_deletion_project/deletions3.html.

Construction of Host Cells Having Altered Levels of Expression of a Target Sequence by Altering Promoter Activity In addition to providing host cells having different levels of target sequence expression as a result of differing copy numbers of the target sequence, the present invention also contemplates other means for altering target sequence expression. For example, transcription levels of the target gene can be altered by, for example, site-specific mutation of the native target gene promoter, or by replacement of the native promoter with a heterologous promoter. Methods for site-specific promoter alteration to affect alteration of transcription levels directed by the promoter (e.g., increase or decrease in transcription relative to the native promoter), as well as methods for introduction of heterologous promoters to drive transcription of a genomic sequence are well known in the art. Exemplary promoters include, but are not limited to, very weak constitutive promoters (e.g., yeast promoter KEX2, regulated promoters (e.g., the yeast promoters CYC1, PGK, and the yeast mating type-specific promoter MFα1), strong constitutive promoters (e g., the yeast promoters TEF1, TDH), and inducible or repressible promoters (e.g., the yeast promoters GAL1, GAL7, GAL10, ADH1, ADH2, MT, PHO5), as well as promoters that provide for temperature-sensitive expression of the target gene. Methods for constructing strains having such heterologous promoters, and methods for inducing and/or maintaining a desired transcription level, and methods for qualitatively and/or quantitatively measuring transcriptional levels are well known in the art.

Exemplary promoters and such methods for their use are described in Nacken et al. 1996 Gene 175:253 (relative transcription levels of KEX2, CYC1, PGK, MFα1, TEF1, and TDH; Mylin et al. 1990 Meth. Enzymol. 185:297 (GAL1, GAL7, and GAL10; also describing use of the GAL expression system to obtain up to 60-fold increase in expression by using a strain containing both the chromosomal wildtype GAL4 gene and an expression cassette consisting of the GAL4 structural gene fused to the GAL10 promoter); Schneider J. C. et al. 1991 Meth. Enzymol. 194:373 (describing the GAL promoter system to provide regulated expression (e.g., using GAL1, which can provide 1000-fold induction in the presence of galactose and repression of expression in the presence of glucose), the ADH1 promoter (which can provide 2-fold to 10-fold repression of expression in the presence of a nonfermentable carbon source), and the PGK promoter (which can provide for 20-fold to 30-fold repression of expression in the presence of a nonfermentable carbon source); Price, V. L. et al. (1990) Meth. Enzymol. 185:308–318 (describing use of the ADH2 promoter to provide regulation of expression by glucose repression); Etcheverry, T. (1990) Meth. Enzymol. 185:319–329 (describing use of the inducible MT promoter); Schena, M. et al. (1991) Meth. Enzymol. 194:389–398 (describing use of the inducible strong promoter PHO5, the high-level constitutive yeast glyceraldehyde-3-phosphate dehydrogenase promoters (see also Schneider J. C. et al, supra), and glucocorticoid-inducible yeast expression vector p2UG in conjunction with the glucocorticoid receptor-encoding vector pG-N795). Additional promoters and expression systems are described in Emr, S. D. (1990) Meth. Enzymol. 185:231; Rose, A. B. et al. (1990) Meth. Enzymol. 185:234–279; Stearns, T. et al. (1990) Meth. Enzymol. 185:280–297; Kingsmen, S. M. et al. (1990) Meth. Enzymol. 185:329–341; Rosenberg, S. et al. (1990) Meth. Enzymol. 185:341–351; and Sledziewski, A. Z. (1990) Meth. Enzymol 185:351–366. Also see generally Goeddel (ed.) 1990 *Expression in Yeast. Methods in Enzymology* 185 Section IV., Academic Press, San Diego, Calif.

Transcription levels can also be increased by introduction of additional copies of the target gene. This can be accomplished by, for example, introduction of an autonomous plasmid, which can be (and preferably is) chromosomally integrated into the genome of the host cell. Such autonomous plasmids are well known in the art and include, but are not limited to, 2- m circle-based vectors (see, e.g., Rose, A. B. et al., supra; Rose, A. B. et al., supra), centromere-based (YCp)vectors, and ARS-based vectors (Rose, A. B. et al., supra). For additional vectors useful in the invention, see Schena et al., supra (describing the pG-1, pG-2, pG-2, and p2UG/pG-N795 expression vector systems). The various promoters mentioned above can be used in conjunction with such plasmids to further increase expression levels of the target gene (see, e.g., Nacken et al., describing that a 3-log difference in expression levels of a gene can be obtained by varying promoter strength only, while introducing a single to high copy number plasmid can add an additional 100-fold increase in expression).

Bioactive Compounds for Analysis

"Bioactive compounds" and "drugs" are used interchangeably herein to denote any chemical compound or agent, e.g., a synthetic compound or compound isolated from natural sources, that alters a biological process in a manner that is detectable using the method of the invention. A "candidate bioactive compound" or "candidate drug" is a natural or synthetic compound that may have the characteristics of a drug through the alteration of a biological process by interaction with a specific target(s).

"Cardidate agents" encompasses numerous chemical classes, and is meant to include synthetic molecules (e.g., small molecule drugs, peptides, or other synthetically produced molecules or compounds, as well as recombinantly produced gene products) as well as naturally-occurring compounds (e.g., polypeptides, endogenous factors present in insulin-producing and/or serotonin-producing cells, hormones, plant extracts, and the like). Candidate agents are also found among biomolecules such as peptides, saccharides, fatty acids, steroids, purines, pyrimidines, derivatives, structural analogs or combinations thereof. Candidate agents that are organic molecules, preferably small organic compounds having a molecular weight of more than 50 and less than about 2,500 daltons. In a preferred embodiment, compounds will have a molecular weight of 50–500 Da. Candidate agents generally comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The method of the invention can be used to identify the gene whose product is the target of any bioactive compound (or candidate bioactive compound) that has a modifying effect that can provide the basis for an in vivo selection. Bioactive compounds (or candidate bioactive compounds) suitable for analysis using the claimed method include, but are not limited to, antibiotics (e.g., antibacterial, bacteriostatic, and antifungal agents), chemotherapeutic agents, agents that affect (inhibit or enhance) a biosynthetic pathway, and the like.

Identification of Bioactive Compounds and/or Target Gene Product-Encoding Sequences The method of the invention is generally accomplished by contacting one or more host cells with a drug or candidate drug for a sufficient period of time. In general, the contacting is for a time that would be sufficient for a compound having a known drug activity to induce a stress response (e.g., to induce expression of a selected stress response gene) in a positive control cell (e.g., in a wildtype cell). The assay can be carried out using a selected set of host cells in parallel or, in embodiments that take advantage of reporter gene constructs that provide for distinctive detectable signals, in a single culture. Methods for culturing host cells, testing of serial dilutions of the drug or candidate drug, and the like, are well known in the art.

After contacting the host cell with the drug or candidate drug, the stress response in the host cell is analyzed either qualitatively or quantitatively. Specifically, induction of the stress response in a wildtype host cell indicates that the candidate agent has drug activity. In general, the stress response is said to be induced when expression of the selected stress response gene is significantly increased in the presence of the drug or candidate drug relative to a level of expression in the absence of the drug or candidate drug. By "significant increase" is meant that the increase in expression of the stress response gene is an increase that is not attributable to sampling or other assay variation. In general, the stress response is said to be induced when expression of the selected stress response gene is greater than 1-fold, usually at least 2-fold greater, generally at least about 2-fold greater in the presence of the stimulus than in the absence of the stimulus. As used herein "wildtype" is an unaltered host cell (i.e., a naturally-occurring host cell). In general, the stress response is determined empirically and generally will be quantitatively measured relative to a control. For example, a weak stress response is, for example, no detectable transcriptional induction of a stress response gene (e.g., hsp26) in a wildtype strain. In one embodiment, the test and control host cells are compared simultaneously. For example, the response of hsp26 in a wildtype strain relative to a deletion strain can be simultaneously compared in a single microtiter well by using different fluorescent reporter polypeptides (e.g., GFP and RFP). Similarly, to identify bioactive compounds, the stress response in untreated host cells is compared to the stress response of host cells treated with the compound. In general, a host cell having altered expression of a gene product(s) is drug-sensitive, and thus provides information about the target gene product of the drug or candidate drug, when the stress response is not induced to a detectable level or induced at a low level when compared to the wildtype cell.

The assay can also be conducted using several different strains of a host cell (e.g., wildtype and recombinant strains altered in expression of different target gene products) in a single culture, with each of the different strains in the culture comprising a reporter construct that provides for a distinct detectable signal for the strain with which it is associated. In one specific embodiment, the reporter constructs of the different strains comprise a different GFP variant (described above), which GFP variant provides a distinct detectable signal. Methods for detecting simultaneous detection of multiple GFP variants in live cells using, for example, fluorescence imaging microscopy or flow cytometry are known in the art (see, e.g., Pepperkok R. et al. (1999) *Curr. Biol.* 9:269–272; Ellenberg R. (1998) *Biotechniques* 25:838–42; 844–6; Lybarger L. et al. (1998) *Cytometry* 31:147–52; Patterson G. H. et al. (1997) *Biophys* 73:2782–90; Yang J. et al. (1996) *Gene* 173(1 Spec No):19–23).

Additional Embodiments of the Invention

The above description of the invention is exemplary, and is not meant to be limiting as to, for example, the methods for detecting induction of the stress response in a host cell, the types of host cells used, the methods and compositions for providing for host cells having varying levels of expression of a target gene, and the like, as such can be varied and remain within scope of the present invention, and such variations will be readily appreciated by the ordinarily skilled artisan upon reading the present specification.

For example, rather than detect changes in stress response gene expression by detection of a reporter polypeptide operably linked to a stress response gene promoter, stress response gene expression can be detected by using methods well known in the art for detecting gene expression levels (e.g., Northern blot, microarray-based, or other solid support-based methods, tailored expression membrane assays, or Taqman assays etc.). Also it will be readily appreciated that increasing the number of stress response genes analyzed (e.g., two or more stress response genes) can provide additional information and/or increase confidence scores of the results obtained relative to detection of a single stress response gene. Assays with multiple stress response genes can be conducted simultaneously using different detectable labels for each gene (e.g., different fluorescent reporters having different excitation and/or emission wavelengths).

The data generated by the invention can be stored in a database, and cumulatively this information can allow for classification of drugs, classification of groups of genes to facilitate elucidation of various pathways, and facilitate identification of additional and/or the more relevant target gene products in a given genetic pathway. In addition, the data in such a database generated using the present invention can be used to identify gene products that cause or mediate toxic response by testing compounds that fail in clinical trials due to such toxicity. Once such gene products are identified, then compounds could be pre-screened for their ability to induce these toxicity genes, and the information used to better design such drugs prior to clinical trials. Furthermore, genes that are associated with drug sensitivity over many experiments can lead to the further understanding of the roles of such gene products, e.g., as drug pumps, enzymes that effect drug metabolism, etc.

Kits

The methods of the invention can be applied in a many different settings and with many different variations, all of which are within the scope of the invention. For example, the compositions described herein can be provided in a kit for use in, for example, a clinical setting. The kit may comprise, control host cells, reagents for detecting expression of a stress response gene, and other materials for conducting the assays described herein.

Rational Therapy

The methods of the invention can be applied in a clinical or veterinarian setting in, for example, the context of determining the resistance or sensitivity of an infecting microorganism to any of a variety of drugs that may be available for treatment of a subject. The subject may be an host that is susceptible to infection by a microorganism, particularly a pathogenic microorganism. The subject may be human or non-human, and can include, but is not necessarily limited to, livestock (e.g., cattle, horses, pigs, chickens, turkeys, and the like), domesticated animals (e.g., dogs, cats, and the like), and other animals for which therapy may be desirable. The microorganism to be screened can be any of a variety of microorganisms in which a stress response can be detected.

Microorganisms thus include, but are not necessarily limited to, pathogenic or non-pathogenic microorganisms, bacteria, yeast, and the like.

A sample suspected of containing an infecting micoorganism is isolated from the subject, which sample may be any appropriate bodily fluid (e.g., blood or blood fractions (e.g., serum, plasma, etc.), urine, saliva, lymph, etc.) or tissue. Optionally, the sample may be processed according to methods known in the art in a manner that provides for better isolation of the infecting microorganisms (e.g., fractionation) with the proviso that the processing step does not result in killing of the microorganism. The sample is then cultured in the presence of a drug, preferably in at least two or more samples, more preferably at least three samples, of increasing drug concentration, e.g., at increasing concentrations ranging from 1-fold to 500-fold, generally from 1-fold to 50-fold to 100-fold, where 1-fold indicates the lowest drug concentration tested. A control sample cultured in the absence of drug can serve as a control.

After an amount of time sufficient to induce a stress response (e.g., based upon a positive control strain), the stress response of the microorganism in the samples is assayed. If the infecting microorganism is resistant to the drug, then higher drug concentrations will be required to induce the stress response of the infecting microorganism (e.g., compared to a control drug sensitive strain). This result would indicate that the drug would be a poor choice for therapy. If a stress response is induced in the infecting microorganism at relatiavely low drug concentrations (e.g., at about the same or lower drug concentration sufficient to induce a stress response in a sensitive control strain), then the drug would be a suitable therapeutic choice. Thus, the method of the invention provides a means for rational therapy, and can provide for more effective therapeutic results.

The stress response assay is not limited to microorganisms. For example, the invention can be used to assess the activity of a particular chemotherapeutic on a tumor sample. In this case a small biopsy is obtained from, for example, a cancerous tumor. In addition, a biopsy can be obtained from the same patient comprised of similar normal tissue as a control. Chemotherapeutics are then be tested on these tissue samples and induced RNA's from stress genes detected. This assay would allow for quickly ascertaining which drug(s) would be the best therapeutic agent for a particular tumor.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

Example 1

Construction of Stress Response Gene Reporter Constructs

Stress response gene reporter constructs are generally constructed as follows: approximately 500 bp to approximately 1,000 bp or more region upstream of the first start codon of the stress gene of interest (the region encompassing the stress response gene promoter) is fused to the coding region of a reporter polypeptide (e.g., GFP-uv in pRS316 (Sikorski and Hieter (1989) *Genetics* 122(1):19–27, Clontech). In a specific exemplary construct, approximately 500 bp of the sequence upstream of the hsp26 gene were ligated to the coding region of GFP-uv in pRS316 to provide for expression of the GFP-uv reporter polypeptide under control of the HSP26 promoter.

Example 2

Construction of Heterozygous Deletion Strains

80% of all heterozygous deletion strains of *Saccharomyces cerevisiae* have been constructed. Heterozygous deletion strains were generated using homologous gene transplacement (Rothstein, R. (1991) *Meth. Enzymol.* 194:281–301) in wild-type diploid strains using standard methods. The resulting heterozygotes carry a deletion in one of the two copies of a given gene. A summary of a few of the strains produced is provided in Table 5.

TABLE 5

Exemplary Heterozygous Deletion Yeast Strains

| Gene | Protein Function | Compound Having Drug Activity |
|---|---|---|
| | Known drugs with known drug targets | |
| HIS3 | enzyme required for histidine biosynthesis | 3-amino-triazole |
| ALG7 | transferase required for Asn-linked glycosylation (Barnes et al. (1984) Mol Cell. Biol. 4:2381; Rine et al. (1983) Proc. Natl. Acad. Sci. USA 80:6750) | tunicamycin |
| TUB2 | -tubulin, essential structural mitotic apparatus component (Shatz et al. (1986)Mol. Cell. Biol. 6:3711) | benomyl |

All strains are transformed with plasmids containing a reporter gene construct for detection of stress response according to the invention. A heterozygous deletion strain that is sensitive to a drug exhibits a reduced stress response relative to a reference strain (e.g., a wildtype strain) and thus is identified as carrying a deletion in a gene product that is the drug's bona ride target, as being otherwise affected (as judged by a decrease in fitness level) by the gene dosage of the bona ride target, or carrying a gene product that is affected by gene dosage of the bona ride target (e.g., the gene product is involved in the same pathway, a parallel pathway, or a pathway involved in drug availability or plays a role in drug resistance.

Example 3

Screening Candidate Agents for Drug Activity by Detection of Stress Response in Wildtype Host Cells The above-described HSP26 construct and a control construct (containing no upstream HSP26 promoter sequence) is transformed into 4 strains: a wildtype strain and strains heterozygous for ALG7, HIS3, and TUB2. The his3 heterozygous strain is sensitive to 3-amino triazole; the alg7 heterozygous strain is sensitive to tunicamycin; and the tub2 heterozygous strain is sensitive to benomyl. The expression of hsp26 activity is then monitored using a fluorimeter. Comparisons (with predicted expectations) are as follows:

TABLE 6

|  | no drug | 3-amino triazole | tunicamycin | benomyl |
|---|---|---|---|---|
| Wildtype | NF | F | F | F |
| his3 heterozygote | NF | NF | F | F |
| alg7 heterozygote | NF | F | NF | F |
| tub2 heterozygote | NF | F | F | NF |

F = fluorescent activity from hsp reporter construct, indicating stress response is induced;
NF = no fluorescence, no induction of stress response Thus expression of stress response genes is expected to be induced in wildtype in response to all three drugs. In contrast, the stress response is expected to be undetectable when the heterozygous strains are mixed with the drugs to which they are sensitive, yet detectable in those same strains when mixed with a drug to which they are not sensitive.

Example 4

Fold Transcriptional Induction of Known Stress Response Genes δ Upon Exposure to Various Stimuli Including Drugs In order to identify stress response genes suitable for use in the methods of the present invention, the induction of various stress response genes was tested using microarrays. Three 50 ml cultures were grown at 30° C., a wildtype strain, an alg7 heterozygous strain, and a ymr007w heterozygous strain (the ymr007w strain has been previously shown to be sensitive to tunicamycin, see Giaever, G. et al. (1999) *Nature Genet.* 21(3):278–283). The wildtype strain was grown in the absence of drug as well as in the presence of 0.5 g/ml tunicamycin at an O.D.600 of 1, or approximately $2 \times 10^7$ cells/ml for one hour. The alg7 and ymr007w heterozygotes were grown in the presence of 0.5 g/ml tunicamycin at an O.D.600 of 1, or approximately $2 \times 10^7$ cells/ml for 1 hour. mRNA was then collected from all four samples using standard techniques. cDNA was then prepared from 20 g of polyadenylated RNA from each sample, using a $dT_{21}$ primer and Superscript II reverse transcriptase (GibcoBRL) according to manufacturer's recommendation. cDNA was fragmented using DNAseI (GibcoBRL), biotinylated using ddATP (NEN) and Terminal Transferase (Boehringer), and hybridized to yeast full genome arrays (Affymetrix) as described in L. Wodicka et al. (1997) *Nature Biotechnol.* 15, 1359–1367. Data was analyzed using Affymetrix software.

The results are summarized in Table 6. The fold induction of the indicated stress response gene is relative to expression levels in the absence of exposure to the indicated stimuli. Conditions other than tunicamycin were obtained from the world wide website of Incyte at proteome.com/databases/YPD, or from other published data (FK506 data from Marton et al. (1998) *Nature Medicine* 4:1293, diauxic shift data from DeRisi, J. et al. (1997) *Science* 278:680–686, heat shock data from Roth, F. P. et al. (1998) *Nature Biotechnol.* 16:939–945 and MMS data from Jelinsky, S. A. and Sampson, L. D. (1999) *Proc. Natl. Acad Sci. USA* 96:1486–1491). Information on various genes and open reading frames were obtained from the Yeast Proteome Database (YPD) (Costanzo, et al. (2000) The Yeast Proteome Database (YPD) and *Caenorhabditis elegans* Proteome Database (WormPD): comprehensive resources for the organization and comparison of model organism protein information. Nucleic Acids Research 28(1): 73–76.

These data show that several different stress response genes demonstrate induction upon exposure to stress, but not in the absence of stress and thus are suitable for use in the present invention. The best candidates will be the ones that are induced in all conditions at a high level.

The results are summarized in Table 7. The fold induction of the indicated stress response gene is relative to expression levels in the absence of exposure to the indicated stimuli for the wildtype strain.

The strains of Table 7 are altered in expression for known stress response genes from yeast. The strains of Table 8 are strains that are altered in expression for an experimentally determined list of genes, identified by their induction of wildtype yeast plus tunicamycin vs. absence of tunicamycin.

The results using strains of known stress response genes from yeast are summarized in Table 7 below.

TABLE 7

| | | Condition: | | | | | |
|---|---|---|---|---|---|---|---|
| ORF name | Gene name | heat shock 39° C. | diauxic shift | MMS 0.1% | TUN 0.6 μM | FK506 50 μM | basal level | gene description |
| YBR072W | HSP26 | 5.6 | 11 | 2.6 | 18 | 7.1 | low | chaperone |
| YOR020C | HSP10 | 2.6 | 2.5 | 1 | 2 | 1 | med | chaperone (mitochondrial) |
| YFL014W | HSP12 | 7.8 | 12 | 4.2 | 2.9 | 1 | med | chaperone |
| YCR021C | HSP30 | 2.2 | 12.5 | 2 | 2 | 2.3 | high | chaperone |
| YDR171w | HSP42 | 1.4 | 12 | 1.5 | 6 | 8.7 | low | chaperone |
| YLR259C | HSP60 | 2.1 | 3.1 | 1 | 1 | 1 | high | chaperone |
| YDR258C | HSP78 | 1.5 | 5.2 | 2.8 | 6.5 | 1 | low | chaperone |
| YPL240C | HSP82 | 2.5 | 2.1 | 1.8 | 2.8 | 1 | low | chaperone |
| YLL026W | HSP104 | 1.9 | 6.2 | 2 | 2 | 1 | med | chaperone |
| YAL005C | SSA1 | 1.6 | 1 | 6.4 | 1 | 1 | med | chaperone |
| YDR059c | UBC5 | 1.3 | 2.7 | 5.5 | 2.1 | 1.1 | low | protein degradation |
| YMR173w | DDR48 | 1 | 3 | 6 | 4.3 | 1 | med | cell stress DNA repair |

These data show that the stress response genes that would be most useful in the present invention are HSP26, HSP12, HSP42, HSP78, HSP82 as they exhibit high levels of induction under several conditions. In addition, the basal level of HSP26 and HSP82 are particularly good candidates for reporters as they are present at low levels in the absence of any stress condition (Craig, E. A. The Molecular and Cellular Biology of the Yeast Saccharomyces: GENE EXPRESSION 501–538 Cold Spring Harbor University Press, Cold Spring Harbor, N.Y., 1990, and as measured signal intensity using Affymetrix confocal scanner where "low" signal intensity is 0–1000, "med" signal intensity is 1000–4000, and "high" signal intensity is >4000).

specificity of the response many of the microarray experiments are performed at lower levels of drug so that the stress response is lowered. In these cases, such as in the case of MMS or FK506 the fold induction levels are likely to be underestimates.compared to that of tunicamycin.

TABLE 8

| ORF name | Gene name | heat shock 39° C. | diauxic shift | MMS 0.1% | TUN 0.6 µM | FK506 50 µm | basal level | gene description |
|---|---|---|---|---|---|---|---|---|
| YBR072W | HSP26 | 5.6 | 11 | 2.6 | 18 | 7.1 | low | chaperone |
| YBL049W | | 6.2 | 1 | 1 | 15 | 6.7 | low | unknown |
| YDR018C | | 1 | 2.6 | 1 | 7.5 | 8.9 | low | Lipid, fatty-acid and sterol metabolism |
| YFL030W | | 1.4 | 4.8 | 5 | 11 | 2 | low | putative transferase |
| YFL059W | SNZ3 | 1 | 1.5 | 2.3 | 25 | 6.3 | low | cell stress |
| YGR043C | | 2.6 | 11.1 | 3.5 | 17 | 2.1 | low | cell stress, transferase (predicted) |
| YHR096C | HXT5 | 1.5 | 8.3 | 1.9 | 200 | 1.6 | low | transporter, MFS family, integral membrane |
| YIL042C | | 1 | 1.6 | 1.4 | 5 | 2.7 | low | transferase (predicted) |
| YIL117C | | 1.4 | 1.5 | 2.3 | 13 | 1 | low | unknown |
| YJL079C | PRY1 | 1.3 | 2.9 | 1 | 13 | 1 | low | cell stress (predicted) |
| YKL107W | | 1 | 2.5 | 1.7 | 112 | 2.5 | low | unknown |
| YLR053C | | 1 | 1 | 1 | 200 | 5.5 | low | unknown |
| YLR121C | YPS3 | 1.2 | 1 | 1 | 15 | 2.5 | low | protein degradation |
| YLR142W | PUT1 | 1 | 5.3 | 1 | 25 | 7.6 | low | amino acid metabolism |
| YMR081C | ISF1 | 1 | 4.8 | 2.9 | 3.5 | 5.4 | low | rna splicing |
| YMR107W | | 1 | 5 | 1 | 79 | 5.9 | low | unknown |
| YNL194C | | 1.1 | 14 | 2.9 | 4.5 | 6.3 | low | cell stress (predicted) |
| YFR026C | | 1 | 1.5 | 2.2 | 20.9 | 3.7 | low | unknown |
| YGL156W | AMS1 | 1.2 | 1.6 | 3.3 | 20 | 2.2 | low | carbohydrate metabolism |
| YJL144W | | 1 | 4.3 | 1.6 | 19.1 | 7.6 | low | unknown |
| YMR040W | | 1 | 1.9 | 1.5 | 12.8 | 1.6 | low | unknown |
| YKL104C | GFA1 | 1 | 1 | 3.3 | 11.2 | 1 | low | carbohydrate metabolism, cell wall maintenance |
| YGR032W | GSC2 | 1.3 | 1.4 | 2.5 | 9.2 | 1.1 | low | carbohydrate metabolism, cell membrane maintenance |
| YLR080W | | 1 | 4.8 | 5.6 | 8.4 | 5.5 | low | unknown |
| YMR174C | PAI3 | 3.2 | 1 | 5.1 | 6.1 | 1 | low | protein degradation, cell stress |
| YLR178C | TSI1 | 4.5 | 6.2 | 5.7 | 6.2 | 1.3 | low | protein degradation, cell stress |
| YMR090W | | 2.2 | 5 | 8 | 5.6 | 1.2 | low | oxidoreductase |
| YLR194C | | 1.4 | 1 | 1 | 5.1 | 1 | med | unknown localizes to cell wall |

These data show that several genes are suitable for use in the invention. HSP26, HSP42, YFL030W, YNL194C in particular are excellent for monitoring stress response as they are induced under all conditions of stress mentioned and are present at low basal levels. It should also be noted that because the stress response often interferes with the In other experiments, the alg 7 and vmr007 heterozygous deletion strains were tested for induction of the stress response in the presence of 0.6 µM tunicamycin for 1 hr (for detailed methods see Example 4). These results are shown in Table 8 below. The numbers indicate the fold induction (positive values) or the fold repression (negative values) relative to that of wildtype expression in the absence of drug.

TABLE 9

| ORF Name | Gene Name | Wild-type no drug | Wildtype tunicamycin 0.6 μM | alg7 heterozygote tunicamycin 0.6 μM | ymr007w heterozygote tunicamycin 0.6 μM |
|---|---|---|---|---|---|
| YBR072W | HSP26 | 1 | 17 | −2.5 | 1.4 |
| YGR043C | | 1 | 17 | −3.5 | −3.5 |
| YHR096C | HXT5 | 1 | 50 | 1 | 1 |
| YLR121C | YPS3 | 1 | 15 | −10 | −10 |
| YMR107W | | 1 | 40 | 1 | 1 |

As can be seen from the results in the above table, neither the alg7 strain nor the ymr007 strain showed any significant induction in stress response. In contrast, a robust stress response was induced in a wildtype strain. This observation supports the assertion that drug sensitive strains will not illicit the normal healthy stress response in the presence of drug.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying a bioactive compound, the method comprising the steps of:
    contacting a yeast host cell containing a heterozygous deletion in a target sequence with a candidate bioactive compound; and
    detecting expression of a stress response gene by the host cell in response to said contacting, wherein the stress response gene by the host cell in response to said contacting, wherein the stress response gene is at least one of HSP26, HSP12, HSP42, HSP78, HSP82, YBR072W, YBL049W, YFL030W, YGR043C, YHR096C, YLR142W, YMR081C, YMR107W, YNL194C, YJL144W, YLR080W, YLR178C or YMR090W;
    wherein detection of no significant increase in expression of the stress response gene as compared to expression of the stress response gene in a control host cell indicates that the candidate bioactive compound has activity as a drug and that the host cell having the heterozygous deletion is sensitive to the drug activity of the compound.

2. The method of claim 1, wherein the yeast host cell comprises a stress response gene reporter construct, wherein expression of the stress response gene reporter construct is indicative of expression of the stress response gene in the yeast host cell.

3. The method of claim 1, wherein at least two more yeast host cells, each having a heterozygous deletion in a different target sequence, are contacted with a candidate bioactive compound, and wherein expression of a reporter gene construct in each yeast host cell provides for a unique detectable signal for detection of stress response gene expression.

4. A method for identifying a target gene product of a bioactive compound, the method comprising the steps of:
    contacting a yeast host cell with a bioactive compound, wherein the host cell is altered in expression of a target gene product; and
    detecting a level of expression of a stress response gene by the host cell in response to said contacting, wherein the stress response gene is at least one of HSP26, HSP12, HSP42, HSP78, HSP82, YBR072W, YBL049W, YFL030W, YGR043C, YHR096C, YLR142W, YMR081C, YMR107W, YNL194C, YJL144W, YLR080W, YLR178C or YMR090W;
    wherein a lower or undetectable level of expression of the stress response gene in the host coil relative to a level of expression in a wildtype host cell exposed to the bioactive compound indicates that the host cell is altered in expression for a target gene product that is involved in mediating resistance or sensitivity to the bioactive compound.

5. The method of claim 4, wherein the yeast host cell comprises a stress response gene reporter construct, wherein expression of the stress response gene reporter construct is indicative of expression of the stress response gene in the yeast host cell.

6. The method of claim 4, wherein at least two or more yeast host cells containing a heterozygous deletion strains are contacted with the bioactive compound, and wherein expression of the reporter gene construct in each yeast host cell provides for a unique detectable for detection of stress response gene expression.

7. The method of claim 3, wherein the yeast host cells are contacted with the candidate bioactive compound in a single culture.

8. The method of claim 6, wherein the yeast host cells are contacted with the bioactive compound drug in a single culture.

* * * * *

UNITED STATES PATENT AND TRADEMARK OFFICE
CERTIFICATE OF CORRECTION

PATENT NO. : 6,743,583 B2
DATED : June 1, 2004
INVENTOR(S) : Ronald W. Davis et al.

It is certified that error appears in the above-identified patent and that said Letters Patent is hereby corrected as shown below:

<u>Column 27,</u>
Lines 45-47, the words "wherein the stress response gene by the host cell in response to said contacting," following the word "contacting" and preceding the word "wherein" should be removed.

<u>Column 28,</u>
Line 31, "coil" should be -- cell --.
Line 45, "the" should be -- a --.
Line 45, -- signal -- should be added following the word "detectable" and preceding the word "for".

Signed and Sealed this

Thirtieth Day of November, 2004

JON W. DUDAS
*Director of the United States Patent and Trademark Office*